(12) United States Patent
Wright et al.

(10) Patent No.: US 8,580,954 B2
(45) Date of Patent: Nov. 12, 2013

(54) FORMULATIONS OF LOW DOSE DICLOFENAC AND BETA-CYCLODEXTRIN

(75) Inventors: Curtis Wright, Rockport, MA (US); Daniel B. Carr, Chestnut Hill, MA (US); Fred H. Mermelstein, Newton, MA (US)

(73) Assignee: Hospira, Inc., Lake Forest, IL (US)

( * ) Notice: Subject to any disclaimer, the term of this patent is extended or adjusted under 35 U.S.C. 154(b) by 85 days.

(21) Appl. No.: 11/689,931

(22) Filed: Mar. 22, 2007

(65) Prior Publication Data

US 2007/0232566 A1     Oct. 4, 2007

Related U.S. Application Data

(60) Provisional application No. 60/786,486, filed on Mar. 28, 2006.

(51) Int. Cl.
*C07H 15/04* (2006.01)
*C07H 3/06* (2006.01)
*C08B 37/10* (2006.01)
*C08B 37/16* (2006.01)

(52) U.S. Cl.
CPC ............... *C07H 15/04* (2013.01); *C07H 3/06* (2013.01); *C08B 37/0015* (2013.01)
USPC .................................................. 536/123.12

(58) Field of Classification Search
USPC .................................................. 514/58, 563
See application file for complete search history.

(56) References Cited

U.S. PATENT DOCUMENTS

| | | | |
|---|---|---|---|
| 4,711,906 A | 12/1987 | von Stetten et al. | |
| 4,727,064 A | 2/1988 | Pitha | |
| 4,764,604 A | 8/1988 | Muller | |
| 4,983,586 A | 1/1991 | Bodor | |
| 5,017,566 A | 5/1991 | Bodor | |
| 5,024,998 A | 6/1991 | Bodor | |
| 5,354,560 A | 10/1994 | Lovrecich | |
| 5,389,681 A | 2/1995 | Galli | |
| 5,449,521 A | 9/1995 | Lovrecich | |
| 5,464,633 A | 11/1995 | Conte | |
| 5,674,854 A | 10/1997 | Bodley et al. | |
| 5,679,660 A * | 10/1997 | Bodley et al. .................. 514/58 |
| 5,681,583 A | 10/1997 | Conte | |
| 5,690,954 A | 11/1997 | Illum | |
| 5,702,724 A | 12/1997 | Stahl | |
| 5,738,874 A | 4/1998 | Conte | |
| 5,747,058 A | 5/1998 | Tipton | |
| 5,747,061 A | 5/1998 | Amselem | |
| 5,785,989 A | 7/1998 | Stanley | |
| 5,811,547 A | 9/1998 | Nakamichi | |
| 5,821,237 A | 10/1998 | Bissett et al. | |
| 5,854,226 A | 12/1998 | Penkler | |
| 5,866,162 A | 2/1999 | Grattan | |
| 5,891,913 A * | 4/1999 | Sallmann et al. .............. 514/567 |
| 5,929,115 A | 7/1999 | Takeuchi | |
| 6,028,222 A | 2/2000 | Dietlin et al. | |
| 6,071,964 A | 6/2000 | Fischer | |
| 6,107,343 A | 8/2000 | Sallmann et al. | |
| 6,294,192 B1 | 9/2001 | Patel | |
| 6,365,180 B1 | 4/2002 | Meyer | |
| 6,407,079 B1 | 6/2002 | Müller et al. | |
| 6,828,299 B2 | 12/2004 | Yang et al. | |
| 6,869,939 B2 | 3/2005 | Mosher et al. | |
| 6,923,988 B2 | 8/2005 | Patel | |
| 7,115,586 B2 | 10/2006 | Loftsson | |
| 7,186,260 B2 | 3/2007 | Hyson | |
| 7,423,028 B2 | 9/2008 | Zoppetti | |
| 7,655,231 B2 | 2/2010 | Shelton et al. | |
| 2002/0012680 A1 | 1/2002 | Patel | |
| 2002/0034539 A1 | 3/2002 | Esposito | |
| 2002/0035264 A1 | 3/2002 | Kararli | |
| 2002/0107265 A1 | 8/2002 | Chen | |
| 2003/0082234 A1 | 5/2003 | Seo | |
| 2003/0113367 A1 | 6/2003 | Penkler | |
| 2003/0139698 A1 | 7/2003 | Hyson | |
| 2003/0232089 A1 | 12/2003 | Singh et al. | |
| 2004/0024044 A1 | 2/2004 | Di Salle | |
| 2004/0072798 A1 | 4/2004 | Naggi | |
| 2004/0137062 A1 | 7/2004 | Chopra | |
| 2004/0151774 A1 | 8/2004 | Pauletti | |
| 2004/0157796 A1 | 8/2004 | Gokarn | |
| 2005/0043481 A1 | 2/2005 | Gref | |
| 2005/0085446 A1 | 4/2005 | Babu | |
| 2005/0095205 A1 | 5/2005 | Krishnamoorthy | |
| 2005/0118272 A1 | 6/2005 | Besse | |

(Continued)

FOREIGN PATENT DOCUMENTS

DE     4207922 A1     9/1993
DE     69820973 T2    12/2004

(Continued)

OTHER PUBLICATIONS

Campbell et al, J. Anasthesia, 1990, 45, 763-66.*
Reer et al., "In Vitro Corneal Permeability of Diclofenac Sodium in Formlations Containing Cyclodextrins Compared to the Commercial Product Voltaren Ophtha" Journal of Pharmaceutical Sciences (1994) vol. 83 No. 9 pp. 1345-1349.*
Cwiertnia et al., "Stability of Diclofenac Sodium in the Inclusion Complex with b-Cyclodextrin in the Solid State" J. Pharm. Pharmacol (1999) vol. 51 pp. 1213-1218.*

(Continued)

*Primary Examiner* — Eric S Olson
(74) *Attorney, Agent, or Firm* — Baker Botts LLP

(57) ABSTRACT

The present invention is directed to a pharmaceutical composition containing a unit dose of a diclofenac compound effective to induce analgesia; and a beta-cyclodextrin compound; wherein the dose of the diclofenac compound is less than 10 mg. The present invention is also directed to methods of treating a subject in need of analgesia with the pharmaceutical compositions of the invention.

4 Claims, 2 Drawing Sheets

(56) References Cited

U.S. PATENT DOCUMENTS

| | | |
|---|---|---|
| 2005/0197303 A1 | 9/2005 | Krishnamoorthy |
| 2005/0203115 A1 | 9/2005 | Sancilio |
| 2005/0238674 A1 | 10/2005 | Penkler et al. |
| 2005/0276841 A1 | 12/2005 | Davis |
| 2006/0024238 A1 | 2/2006 | Barth |
| 2006/0121085 A1 | 6/2006 | Warren |
| 2006/0134095 A1 | 6/2006 | Ito |
| 2006/0188530 A1 | 8/2006 | Yoo |
| 2006/0210604 A1 | 9/2006 | Dadey |
| 2006/0211599 A1 | 9/2006 | Suzuki |
| 2007/0049552 A1 | 3/2007 | Babu |
| 2007/0116730 A1 | 5/2007 | Simmons |
| 2007/0207222 A1 | 9/2007 | Yu |
| 2007/0219170 A1 | 9/2007 | Samson |
| 2007/0232566 A1 | 10/2007 | Wright |
| 2007/0232567 A1 | 10/2007 | Wright |
| 2008/0171014 A1 | 7/2008 | Wu |
| 2008/0200533 A1 | 8/2008 | Krishnan |
| 2008/0220441 A1 | 9/2008 | Birnbaum |
| 2009/0292022 A1 | 11/2009 | Kowalski et al. |
| 2011/0218247 A1 | 9/2011 | Wright et al. |
| 2012/0142779 A1 | 6/2012 | Penkler et al. |

FOREIGN PATENT DOCUMENTS

| | | | |
|---|---|---|---|
| DE | 69434356 T2 | 5/2006 | |
| EP | 0268215 | 5/1988 | |
| EP | 0335545 A2 | 10/1989 | |
| EP | 371431 A2 | 6/1990 | |
| EP | 446753 A1 | 9/1991 | |
| EP | 0519428 A2 | 12/1992 | |
| EP | 598337 A2 | 5/1994 | |
| EP | 647451 A1 | 4/1995 | |
| EP | 0658347 A2 | 6/1995 | |
| EP | 807434 A1 | 11/1997 | |
| EP | 868915 A1 | 10/1998 | |
| EP | 1004318 A2 | 5/2000 | |
| EP | 862414 B1 | 12/2001 | |
| EP | 833618 B1 | 4/2002 | |
| EP | 730443 B1 | 5/2002 | |
| EP | 01219304 A2 | 7/2002 | |
| EP | 1219306 A1 | 7/2002 | |
| EP | 729748 B1 | 2/2003 | |
| EP | 0658347 | 8/2003 | |
| EP | 0701449 | 8/2003 | |
| EP | 917457 B1 | 1/2004 | |
| EP | 792147 B1 | 3/2004 | |
| EP | 1574221 | 9/2005 | |
| EP | 1574221 A1 * | 9/2005 | ............. A61K 47/18 |
| EP | 1595936 A1 | 11/2005 | |
| EP | 1609481 A1 | 12/2005 | |
| EP | 1681065 A1 | 7/2006 | |
| EP | 1767219 A2 | 3/2007 | |
| EP | 1524968 B1 | 12/2007 | |
| EP | 1515729 B1 | 2/2008 | |
| EP | 1677761 B1 | 4/2008 | |
| EP | 1967186 A1 | 9/2008 | |
| EP | 1974751 A1 | 10/2008 | |
| GB | 2 230 440 | 10/1990 | |
| GB | 2417900 A | 3/2006 | |
| JP | 59-084821 | 5/1984 | |
| JP | 62138437 A | 6/1987 | |
| JP | 1-287094 | 11/1989 | |
| JP | 06-16547 | 1/1994 | |
| JP | 7196484 A | 8/1995 | |
| JP | 7252144 A | 10/1995 | |
| JP | 9-48737 | 2/1997 | |
| JP | 2006-502185 | 1/2006 | |
| WO | WO 90/02141 A1 | 3/1990 | |
| WO | WO 92/00725 A1 | 1/1992 | |
| WO | WO9203122 A1 | 3/1992 | |
| WO | WO9406416 A1 | 3/1994 | |
| WO | WO9428936 A1 | 12/1994 | |
| WO | WO9501781 A1 | 1/1995 | |
| WO | WO9504528 A2 | 2/1995 | |
| WO | WO9507104 A1 | 3/1995 | |
| WO | WO9511669 A1 | 5/1995 | |
| WO | WO9532737 A1 | 12/1995 | |
| WO | WO9611003 A1 | 4/1996 | |
| WO | WO9614839 A1 | 5/1996 | |
| WO | WO9622088 A1 | 7/1996 | |
| WO | WO97/10805 * | 11/1996 | ............... A61K 9/00 |
| WO | WO 96/41646 | 12/1996 | |
| WO | WO9641617 A1 | 12/1996 | |
| WO | WO 97/10805 A1 | 3/1997 | |
| WO | WO9735568 A2 | 10/1997 | |
| WO | WO9851280 A1 | 11/1998 | |
| WO | WO9936060 A1 | 7/1999 | |
| WO | WO0050007 A1 | 8/2000 | |
| WO | WO0059475 A1 | 10/2000 | |
| WO | WO 00/66099 | 11/2000 | |
| WO | WO0071098 A1 | 11/2000 | |
| WO | WO0113897 A1 | 3/2001 | |
| WO | WO0128555 A1 | 4/2001 | |
| WO | WO 01/41760 | 6/2001 | |
| WO | WO0145742 A1 | 6/2001 | |
| WO | WO0180797 A1 | 11/2001 | |
| WO | WO0205815 A1 | 1/2002 | |
| WO | WO0220020 A1 | 3/2002 | |
| WO | WO02053188 A1 | 7/2002 | |
| WO | WO02072106 A2 | 9/2002 | |
| WO | WO 03/018009 | 3/2003 | |
| WO | WO03033025 A2 | 4/2003 | |
| WO | WO 03/063824 | 8/2003 | |
| WO | WO 03/095498 | 11/2003 | |
| WO | WO03097011 A1 | 11/2003 | |
| WO | WO03105867 A1 | 12/2003 | |
| WO | WO2004041118 A2 | 5/2004 | |
| WO | WO2004081196 A2 | 9/2004 | |
| WO | WO2004089418 A1 | 10/2004 | |
| WO | WO2005044231 A1 | 5/2005 | |
| WO | WO2005074887 A2 | 8/2005 | |
| WO | WO2005077336 A1 | 8/2005 | |
| WO | WO2005086763 A2 | 9/2005 | |
| WO | WO 2005/092387 * | 10/2005 | ............. A61K 47/18 |
| WO | WO2005092387 A1 | 10/2005 | |
| WO | WO2005120578 A2 | 12/2005 | |
| WO | WO2005123193 A2 | 12/2005 | |
| WO | WO2006007753 A1 | 1/2006 | |
| WO | WO2006041942 A2 | 4/2006 | |
| WO | WO2006082588 A2 | 8/2006 | |
| WO | WO2007004236 A1 | 1/2007 | |
| WO | WO2007005608 A2 | 1/2007 | |
| WO | WO2007044062 A1 | 4/2007 | |
| WO | WO2007052289 A2 | 5/2007 | |
| WO | WO2007059591 A1 | 5/2007 | |
| WO | WO2007061828 A2 | 5/2007 | |
| WO | WO2007103435 A2 | 9/2007 | |
| WO | WO2007103687 A2 | 9/2007 | |
| WO | WO2007106381 A2 | 9/2007 | |
| WO | WO2007112272 A2 | 10/2007 | |
| WO | WO2007112274 A2 | 10/2007 | |
| WO | WO2008006216 A1 | 1/2008 | |
| WO | WO2008040534 A2 | 4/2008 | |
| WO | WO2008071851 A1 | 6/2008 | |
| WO | WO2008074087 A1 | 6/2008 | |
| WO | WO2008076703 A1 | 6/2008 | |
| WO | WO2008115572 A1 | 9/2008 | |
| WO | WO2008127271 A2 | 10/2008 | |
| WO | WO2008127291 A2 | 10/2008 | |
| WO | WO2008133982 A1 | 11/2008 | |
| WO | WO2008134600 A1 | 11/2008 | |
| WO | WO2008134601 A1 | 11/2008 | |

OTHER PUBLICATIONS

Routes of Administration Requirirng Sterile Formulations, The Pharmaceutics and Compounding Laboratory, downloaded Aug. 20, 2012, from http://pharmlabs.unc.edu.*

Jambhekar et al., "The physicochemical characteristics and bioavailability of indomethacin from beta-cyclodextrin, hydroxyethyl-beta-cyclodextrin, and hydroxypropyl-beta-cyclodextrin complexes", (2004), Int. J. Pharm., 270(1-2):149-66.

(56) References Cited

OTHER PUBLICATIONS

Ocana et al., "Potassium Channels and Pain: Present Realities and Future Opportunities", (2004), European Journal of Pharmacology, (2004), 500:203-219.
Reer et al., "In Vitro Corneal Permeability of Diclofenac Sodium in Formulations Containing Cyclodextrins Compared to the Commercial Product Voltraren Ophtha", Journal of Pharmaceutical Sciences, (1994), 83(9):1345-1349.
Uekama, "Cyclodextrin Inclusion Compounds: Effects on Stability and Bio-Pharmaceutical Properties", Elsevier Science Publishers B.V. (Biomedical Division), (1987), pp. 181-193.
Backensfeld et al., "Interaction of NSA with Cyclodextrins and Hydroxypropyl Cyclodextrin Derivatives", Int. J. Pharm., (1991), 74:85-93.
Backensfeld et al., "Solubilization and Stabilization of Non-Steroidal Antirheumatics with Cyclodextrins and Cyclodextrin Ethers", Arch. Pharm., (1990), 323:690.
Orienti et al., "Inclusion Complexes Between Non Steroidal Antiinflammatory Drugs and beta-Cyclodextrin", Dur. J. Pharm. Biopharm., (1991), 37(2):110-112.
Orienti et al., "Availability of NSAIDH beta-Cyclodextrin Inclusion Complexes", Arch. Pharm. (Weinheim), (1989), 322:207-211.
Nekroshus et al., English Abstract of Russian Article, "Preparing the Inclusion Compounds Orthophen and Indomethcin with .beta.-Cyclodextrin and their Derivatographic Analysis", Farmatsiya Moscow, (1989), 38:29-34.
Devi et al., "Albumin Microspheres and beta-Cyclodextrin Inclusion Complex Containing Diclofenac Sodium", Ind. J. Pharm. Sci, (1992), 54:259-261.
Kurozumi et al., "Inclusion Compounds of Non-Steroidal Antiinflammatory and Other Slightly Water Soluble Drugs with alpha- and beta-Cyclodextrins in Powdered Form," Chem. Pharm. Bull., (1975), 23:3062-3068.
Otagiri et al., "Comparative Study on Inclusion Complexation of beta-Cyclodextrin and Tri-O-Methyl-beta-Cyclodextrin with Several Drugs in Aqueous Solution", Acta Pharm. Suec., (1984), 21:357-366.
Ikeda et al., "Inclusion Complexes of beta-Cyclodextrin with Antiinflammatory Drugs Fenamates in Aqueous Solution", Chem. Pharm. Bull., (1975), 23(1):201-208.
Pose-Vilarnovo et al., "Modulating Drug Release With Cyclodextrins in Hydroxypropyl methylcellulose gels and tablets", Journal of Controlled Release, (2004), 94:351-363.
Gunnison et al., "Sulfite Hypersensitivity, A Critical Review", CRC Critical Reviews in Toxicology, (1987), 17(3):185-214.
Reed et al., "Lysis of Human Red Blood Cells in the Presence of Various Cosolvents", Journal of Parenteral Science and Technology, (1985), 39(2):64-69.
European Search Report (Appln No. 04257437.6-1219, dated Jun. 15, 2005).
Kasrarian et al., "Developing an injectable formula containing an oxygen-sensitive drug: a case study of danofloxacin injectable" Pharm. Dev. Technol., (1999), 4(4):475-80.
Heaney et al., "Sequential clot strength analyses following diclofenac in pediatric adenotonsillectomy", Pediatric Anethesia, (2007), 17:1078-1082.
Mammen et al., "PFA-100™ System: A New Method for Assessment of Platelet Dysfunction", Seminars in Thrombosis and Hemostasis, (1998), 24(2):195-202.
Kundu et al., "Description of an In Vitro Platelet Function Analyzer—PFA-100™", Seminars in Thrombosis and Hemostasis, (1995), 21(2):106-112.
McCabe et al., "Assessment of the antiplatelet effects of low to medium dose aspirin in the early and late phase after ischaemic stroke and TIA", Platelets, (2005), 16(5):269-280.
Munsterhjelm et al., "Propacetamol augments inhibition of platelet function by diclofenac in volunteers", British Journal of Anaesthesia, (2003), 91(3):357-362.
Coakley et al., "Use of the platelet function analyser (PFA-100®) to quantify the effect of low dose aspirin in patients with ischaemic heart disease", Anaesthesia, (2005), 60:1173-1178.

Blaicher et al., "Effect of non-selective, non-steroidal anti-inflammatory drugs and cyclo-oxygenase-2 selective inhibitors on the PFA-100 closure time", Anaesthesia, (2004), 59:1100-1103.
Niemi et al., "Comparison of the effect of intravenous ketoprofen, ketorolac and diclofenac on platelet function in volunteers", Acta. Anaesthesiol. Scand., (1997), 41:1353-1358.
Rorarius et al., "Diclofenac versus indomethacin given as intravenous infusions: their effect on haemodynamics and bleeding time, and side-effects in healthy subjects", Annals of Clinical Research, (1985), 17:306-309.
Perttunen et al., "I.V. Diclofenac in post-thoracotomy pain", British Journal of Anaesthesia, (1992), 68:474-480.
Laitinen et al., "Intravenous Diclofenac Coupled with PCA Fentanyl for Pain Relief after Total Hip Replacement", Anesthesiology, (1992), 76:194-198.
Legeby et al., "Analgesic efficacy of diclofenac in combination with morphine and paracetamol after mastectomy and immediate breast reconstruction", Acta. Anaethesiol. Scand., (2005), 49:1360-1366.
Hyrkäs, "Effect of Preoperative Single Doses of Diclofenac and Methylprednisolone on Wound Healing", Scand. J. Plast. Reconstr. Hand Surg., (1994), 28:275-278.
Rorarius et al., "Effects of peri-operatively administered diclofenac and indomethacin on blood loss, bleeding time and plasma prostandoids in man", European Journal of Anaesthesiology, (1989), 6:335-342.
Laitinen et al., "Effect of a non-steriodal anti-inflammatory drug, diclofenac, on haemostasis in patients undergoing total hip replacement", Acta. Anaesthesiol. Scand., (1992), 36:486-489.
Thiagarajan et al. "Blood loss following tonsillectomy in children", Anaesthesia, (1993), 47:132-135.
Power et al., "Platelet function after intramuscular diclofenac", Anaesthesia, (1990), 45:910-919.
Schmidt et al., "Preoperative rectal diclofenac versus paracetamol for tonsillectomy: effects on pain and blood loss", Acta. Anaesthesiol. Scand., (2001), 45:48-52.
Robinson et al., "Diclofenac and post-tonsillectomy haemorrhage", Clin. Otolatryngol., (1994), 19:344-345.
Robinson, "Correspondence: Diclofenac and post tonsillectomy haemorrhage", Clin. Otolatryngol., (1995), 20:483-484.
Sia et al., "Combination of suppository diclofenac and intravenous morphine infusion in post-caesarean section pain relief—a step towards balanced analgesia?", Singapore Med. J., (1997), 38(2):68-70.
Munsterhj elm et al., "Characterization of inhibition of platelet function by paracetamol and its interaction with diclofenac in vitro", Acta. Anaesthesiol. Scand., (2005), 49(6):840-846.
Dahl et al., "High-dose diclofenac for postoperative analgesia after elective caesarean section in regional anaesthesia", Int. J. Obstet. Anesth., (2002), 11(2):91-94.
Bricker et al., "Peri-operative blood loss and non-steriodal anti-inflammatory drugs: an investigation using diclofenac in patients undergoing transurethral resection of the prostate", European Journal of Anaesthesiology, (1987), 4:429-434.
Nordbladh et al., "Analgesia in tonsillectomy: a double-blind study on pre and post-operative treatment with diclofenac", Clin. Otolaryngol., (1991), 16:554-558.
Pilotto et al., "The risk of upper gastrointestinal bleeding in elderly users of aspirin and other non-steroidal anti-inflammatory drugs: the role of gastroprotective drugs", Aging Clin. Exp. Res., (2003), 15(6):494-499.
Kokki, "Nonsteroidal anti-inflammatory drugs for postoperative pain: a focus on children", Paediatr. Drugs, (2003), 5(2):103-123.
Lewis et al., "Dose-response relationships between individual nonaspirin nonsteroidal anti-inflammatory drugs (NANSAIDs) and serious upper gastrointestinal bleeding: a meta-analysis based on individual patient data", Clin. Pharmacol., (2002), 54:320-326.
Mandell, "General Tolerability and Use of Nonsteroidal Anti-Inflammatory Drugs", The American Journal of Medicine, (1999), 107(6A):72S-76S.
Saray et al., "Diclofenac and metamizol in postoperative analgesia in plastic surgery", Acta. Chirurgiae. Plasticae., (2001), 43(3):71-76.

(56) References Cited

OTHER PUBLICATIONS

Anderson et al., "Diclofenac in Combination With Opiate Infusion After Joint Replacement Surgery", Anaesth. Intens. Care, (1991), 19:535-538.

Mendham et al., "Comparison of diclofenac and tenoxicam for postoperative analgesia with and without fentanyl in children undergoing adenotonsillectomy or tonsillectomy", Paediatric Anaesthesia, (1996), 6:467-473.

Hegi et al., "Effect of rofecoxib on platelet aggregation and blood loss in gynaecological and breast surgery compared with diclofenac", British Journal of Anaesthesia, (2004), 92(4):523-531.

Tai et al., "Comparison of controlled-release ketoprofen and diclofenac in the control of post-surgical dental pain", Journal of the Royal Society of Medicine, (1992), 85:16-18.

O'Hanlon et al., "A comparison of the effect of intramuscular diclofenac, ketorolac or piroxicam on post-operative pain following laparoscopy", European Journal of Anaesthesiology, (1996), 13:404-407.

Leese et al., "Valdecoxib Does Not Impair Platelet Function", American Journal of Emergency Medicine, (2002), 20(4):275-281.

Campbell et al., "Intravenous diclofenac sodium", Anaethesia, (1990), 45:763-766.

Sun et al., "Effects of Epidural Morphine and Intramuscular Diclofenac Combination in Postcesarean Analgesia: A Dose-Range Study", Anasth. Analg., (1993), 76:284-288.

Ejnell et al., "Treatment of postoperative pain with diclofenac in uvulopalatopharyngoplasty", British Journal of Anaesthesia, (1992), 68:76-80.

Van Hecken et al., "Comparative Inhibitory Activity of Rofecoxib, Meloxicam, Diclofenac, Ibuprofen, and Naproxen on COX-2 versus COX-1 in Healthy Volunteers", J. Clin. Pharmacol., (2000), 40:1109-1120.

Graham, "COX-2 Inhibitors, Other NSAIDs, and Cardiovascular Risk", JAMA., (2006), 296.

McGettigan et al., "Cardiovascular Risk and Inhibition of Cyclooxygenase. A Systematic Review of the Observational Studies of Selective and Nonselective Inhibitors of Cyclooxygenase 2", JAMA, (2006), 296(13):E1-E12.

Yee et al., "Platelet hyperactivity generalizes to multiple forms of stimulation", Journal of Thrombosis and Haemostasis, (2006), 4:2043-2050.

Romsing et al., "Diclofenac or acetaminophen for analgesia in paediatric tonsillectomy outpatients", Acta. Anaesthesiol. Scand., (2000), 44(3):291-295.

Final Study Report, Randomized, double-blind, placebo and comparator controlled, single-dose, parallel-group comparison of the analgesic efficacy and safety of intravenous DIC075V (diclofenac sodium) injection, ketorolac tromethamine, and placebo following study (Jun. 4, 2009).

Menasse et al, *Scand. J. Rheumatol. Suppl.* 22:5-16 (1978).

Maier et al., *Rheumatol. Rehabil.* Suppl. 2:11-21 (1979).

*Adis Drugs Monograph on Diclofenac* (2008).

Todd et al., *Drugs* 35(3): 244-85 (1988).

Brogden et al., *Drugs* 20(1): 24-48 (1980).

FDA product label for diclofenac, http://www.drugs.com/pro/diclofenac.html, Aug. 2006.

Seymour et al., *Eur. J. Clin. Pharmacol.* 56:447-452 (2000).

Hersh et al, *Clin. Ther.* 26(8):1215-27 (2004).

European Search Report for EP Patent Application No. 07759156.

Reddy et al. "Beta Cyclodextrin Complexes of Celecoxib: Molecular Modeling, Characterization, and Dissolution Studies," AAPS Pharm. Sci., vol. 6, No. 1, 7, Mar. 5, 2005, pp. 1-9.

Barbato F. et al. "Diclofenac beta-Cyclodextrin Binary Systems: A Study in Solution and in the Solid State," J. Inclusion Phenomena and Macrocyclic Chem. vol. 46, Aug. 2003, pp. 179-185.

Hawley's Condensed Chemical Dictionary, 1997, p. 603.

Non-Final Office Action issued on Dec. 31, 2009 on U.S. Appl. No. 11/689,939.

Response to Final Office Action filed Oct. 28, 2009 on U.S. Appl. No. 11/689,939.

Final Office Action issued on Apr. 29, 2009 on U.S. Appl. No. 11/689,939.

Response to Non-Final Office Action filed Jan. 7, 2009 on U.S. Appl. No. 11/689,939.

Non-Final Office Action issued on Sep. 19, 2008 on U.S. Appl. No. 11/689,939.

U.S. Appl. No. 11/689,939, Apr. 1, 2011 Final Office Action.

U.S. Appl. No. 11/689,939, Feb. 10, 2011 Response to Non-Final Office Action.

U.S. Appl. No. 11/689,939, Sep. 10, 2010 Non-Final Office Action.

U.S. Appl. No. 11/689,939, Jul. 1, 2010 Examiner's Interview Summary.

U.S. Appl. No. 11/689,939, Jun. 23, 2010 Response to Non-Final Office Action.

FDA label for BEXTRA® Valdecoxib tablets, revised Nov. 2004, dowloaded from www.fda.gov.

U.S. Appl. No. 13/106,697, filed May 12, 2011.

U.S. Appl. No. 13/106,697, Jul. 18, 2012 Non-Final Office Action.

Nagarsenker et al., "Solid dispersion of hydroxyproply beta-cyclodextrin and ketrolac: enhancement of in-vitro dissolution rates, improvement in anti-inflammatory activity and reduction in ulcerogenicity in rats", *Journal of Pharmacy and Pharmacology*, 52(8):949-956, Aug. 2000.

U.S. Appl. No. 11/689,939, Aug. 27, 2012 Non-Final Office Action.

Japanese Office Action dated Aug. 29, 2012 from Japanese Application No. 2009-503166, (corresponding to U.S. Appl. Nos. 11/689,931 and 13/106,697).

Kore, et al,, "Toxicology of Nonsteroidal Antiinflammatory Drugs", *Veterinary Clinics of North America, Small Animal Practice*, 20(2):419-430 (1990).

Gazarian, et al., "Safe use of NSAIDs in infants and children", *Medicine Today*, 7(11):71-73 (2006).

Rekkas, et al., "Oral and intramuscular absorption of ibuprofen after administration of a freeze-dried ibuprofen 2-hp-beta-CD complex in dogs", *Proceedings of the International Symposium on Controlled Release of Bioactive Materials*, 24:557-558 (1997).

FDA Orange Book entry for ibuprofen intravenous solution, downloaded Aug. 20, 2012 from http://www.accessdata.fda.gov.

FDA Orange Book entry for ketorolac injectable solution, downloaded Aug. 20, 2012 from http://www.accessdata.fda.gov.

U.S. Appl. No. 13/153283, filed Jun. 3, 2011.

U.S. Appl. No. 10/999,155, filed Nov. 30, 2004.

U.S. Appl. No. 13/153,283, Nov. 29, 2012 Non-Final Office Action.

U.S. Appl. No. 13/106,697, Dec. 31, 2012 Final Office Action.

U.S. Appl. No. 13/106,697, Nov. 19, 2012 Response to Non-Final Office Action.

U.S. Appl. No. 10/999,155, Aug. 16, 2011 Notice of Abandonment.

U.S. Appl. No. 10/999,155, Dec. 6, 2010 Final Office Action.

U.S. Appl. No. 10/999,155, Nov. 4, 2010 Response to Non-Final Office Action.

U.S. Appl. No. 10/999,155, May 5, 2010 Non-Final Office Action.

U.S. Appl. No. 10/999,155, Mar. 18, 2010 Amendment and Request for Continued Examination (RCE).

U.S. Appl. No. 10/999,155, Aug. 18, 2009 Notice of Appeal.

U.S. Appl. No. 10/999,155, Feb. 20, 2009 Final Office Action.

U.S. Appl. No. 10/999,155, Sep. 15, 2008 Response to Non-Final Office Action.

U.S. Appl. No. 10/999,155, Jun. 11, 2008 Non-Final Office Action.

U.S. Appl. No. 10/999,155, Oct. 26, 2007 Response to Non-Final Office Action.

U.S. Appl. No. 10/999,155, Jul. 26, 2007 Non-Final Office Action.

Ammon, et al., "Diclofenac does not Interact with Codeine Metabolism in Vivo: A Study of Healthy Volunteers", *BMC Clinical Pharmacology*, 2(2):1-10 (2002).

Christensen, et al., "A Double-Blind Placebo-Controlled Comparison of a Novel Formulation of Intravenous Diclofenac and Ketorolac for Postoperative Third Molar Extraction Pain", *Anesth. Prog.*, 58:73-81 (2011).

Eddaoudi, et al., "Solubilities of the Cyclodextrins in the Presence of Transition Metal Salts", *Journal of Inclusion Phenomena and Molecular Recognition in Chemistry*, 26:133-151 (1996).

(56) References Cited

OTHER PUBLICATIONS

Eyjolfsson, "Diclofenac Sodium: Oxidative Degradation in Solution and Solid State", *Drug Development and Industrial Pharmacy*, 26(4):451-453 (2000).

Gaudiano, et al., "RP-HPLC Study of the Degradation of Diclofenac and Piroxican in the Presence of Hydroxyl Radicals", *Journal of Pharmaceutical and Biomedical Analysis*, 32:151-158 (2003).

Jansook, et al. "CD as Solubilizers: Effects of Excipients and Competing Drugs", *Int. J. Pharm*, 379(1):32-40 (2009).

Ledwidge, et al., "Effects of Surface Active Characteristics and Solid State Forms on the pH Solubility Profiles of Drug-Salt Systems", *Int. J. Pharm.*, 174(1-2):187-200 (1998).

Loftsson, et al., "Pharmaceutical Applications of Cyclodextrins: 1. Drug Solubilization and Stabilization", *Journal of Pharmaceutical Sciences*, 85(10):1017-1025 (1996).

Martin Del Valle, et al., "Cyclodextrins and Their Uses: A Review", *Process Biochemistry*, 39:1033-1046 (2004).

International Search Report and Written Opinion for PCT/IB2004/003918, dated Jun. 15, 2005.

International Preliminary Report on Patentability for PCT/IB2004/003918, dated Sep. 13, 2006.

International Search Report and Written Opinion for PCT/US2005/007354, dated Dec. 22, 2005.

International Preliminary Report on Patentability for PCT/US2005/007354, dated Sep. 13, 2006.

International Search Report and Written Opinion for PCT/US2012/047453, dated Oct. 4, 2012.

U.S. Appl. No. 13/106,697, Apr. 30, 2013 Amendment and Request for Continued Examination (RCE).

U.S. Appl. No. 13/153,283, Apr. 29, 2013 Response to Non-Final Office Action.

\* cited by examiner

FORMULATIONS OF LOW DOSE DICLOFENAC AND BETA-CYCLODEXTRIN

CROSS-REFERENCE TO RELATED APPLICATIONS

This application claims priority under 35 U.S.C. §119, based on U.S. Provisional Application Ser. No. 60/786,486, filed Mar. 28, 2006, the disclosure of which is incorporated herein by reference in its entirety.

FIELD OF THE INVENTION

The present invention is directed to pharmaceutical compositions and methods of treating a subject in need of analgesia with pharmaceutical compositions which contain diclofenac and beta-cyclodextrin. Specifically, the compositions contain low doses of diclofenac, namely less than 10 mg.

BACKGROUND OF THE INVENTION

Diclofenac is a well-known non-steroidal anti-inflammatory drug ("NSAID") used in acute and chronic pain in both parenteral and oral dosage forms. Oral dosages range from 100-200 mg/day, while parenteral dosages range from 75-150 mg/day (1-2 mg/kg/day) by either infusion or intermittent (divided) doses. Toxicity of oral and parenteral forms are well known, with gastro-intestinal, hemorrhagic, renal, hepatic, cardiovascular and allergic (anaphylactic and severe dermal allergy) adverse events being most significant.

Parenteral use of diclofenac has been limited due to limited solubility, such that parenteral preparations have had to include non-polar solvents in order to achieve concentrations (75 mg/3 ml) which would allow intra-muscular (IM) administration of the desired dose. This solubility has limited the parenteral use to IM use and/or slow intravenous (IV) administration of diluted (100-500 ml diluent) product.

U.S. Pat. No. 5,679,660 and co-pending application Ser. No. 10/999,155, filed Nov. 30, 2004, published as U.S. 2005/0238674 A1 on Oct. 27, 2005, both of which are incorporated by reference, disclose novel formulations of diclofenac with hydroxypropyl-beta-cyclodextrin, which allows a more concentrated preparation and thus rapid intravenous administration. The data show that the more concentrated the diclofenac/beta-cyclodextrin formulation, the faster onset of action over current products.

Other than ease of administration and more rapid onset of action, consequent on the improvements in the pharmaceutical formulation, no other advantages were observed. The present invention arises, in part, from the surprising discovery that formulating a non-steroidal anti-inflammatory drug with beta-cyclodextrin not only improves solubility and stability of the drug, it also increases efficacy.

SUMMARY OF THE INVENTION

The present invention relates to a pharmaceutical composition comprising a unit dose of a diclofenac compound effective to induce analgesia; and a beta-cyclodextrin compound, in which the dose of the diclofenac compound is less than 10 mg. This dose is less than any effective dose previously reported or even suggested for a formulation of a diclofenac and a beta-cyclodextrin compound. The diclofenac compound can be a diclofenac salt, e.g., diclofenac sodium, as exemplified infra. The beta-cyclodextrin compound can be 2-hydroxypropyl-beta-cyclodextrin, as exemplified infra.

The pharmaceutical composition may further comprise a stabilizer, such as monothioglycerol.

In specific embodiments, the pharmaceutical composition provides a dose of diclofenac of about 9.4 mg, less than about 5 mg, and even about 3.75 mg.

The invention further provides a method for treating a mammal in need of analgesia by administering a pharmaceutical composition of the invention, as set forth above. In a specific embodiment, the mammal is a human. In particular, the pharmaceutical composition can be administered intravenously.

The advantageous methods of the invention pertain to other formulations as well. Thus, the invention provides a method for treating a mammal in need of analgesia by administering a pharmaceutical composition comprising a dosage of a diclofenac compound effective to induce analgesia; and a beta-cyclodextrin compound, in which the dosage of the diclofenac compound is less than about 1.3 mg/kg per day. In particular embodiments, the dosage of diclofenac is less than 0.65 mg/kg per day, less than 0.33 mg/kg per day, or less than 0.165 mg/kg per day.

In another embodiment of the methods of treatment, the invention provides a method for treating a mammal in need of analgesia by administering a pharmaceutical composition comprising a dosage of a diclofenac compound effective to induce analgesia; and a beta-cyclodextrin compound, wherein the dosage of the diclofenac compound is less than a minimum approved dose for a particular route of administration. The dose of the diclofenac compound can have the same efficacy of pain relief as the minimum approved dose, or it can have from about 70% to about 100% or from about 40% to about 70% of the efficacy of pain relief as the minimum approved dose. In addition, the dose of the diclofenac compound can have the same duration of pain relief as the minimum approved dose, or it can have from about two-thirds to the same duration of pain relief, or from about one-third to about two-thirds of the duration of pain relief, as the minimum approved dose.

DETAILED DESCRIPTION OF THE INVENTION

Figure 1:
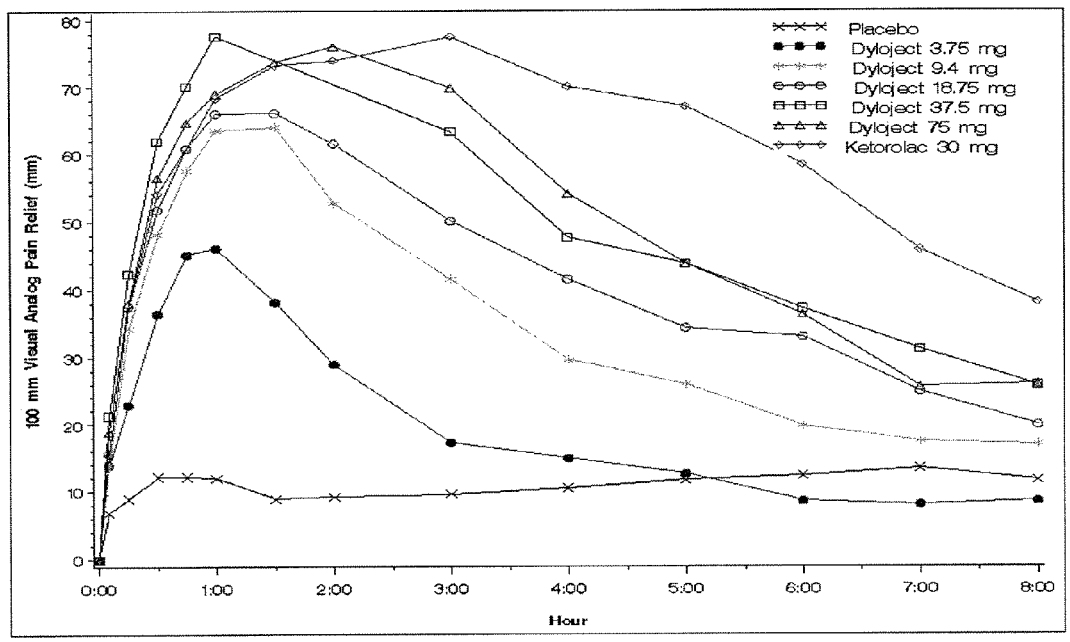
FIG. 1 contains a graphical representation of the 100 mm visual analog pain relief (mm) afforded to patients over time (hours) based on the formulation strengths administered. The tested formulations include placebo, 3.75 mg Dyloject, 9.4 mg Dyloject, 18.75 mg Dyloject; 37.5 mg Dyloject, 75 mg Dyloject, and 30 mg Ketorolac.

The present invention provides formulations of a diclofenac compound with a beta-cyclodextrin compound. These formulations unexpectedly provide for significant efficacy and duration of pain relief at a lower dose than the current recommended doses of the diclofenac. More particularly, at a reduced dose and dosage, the formulation provides the same level of efficacy and the same duration of analgesia as at the minimum approved dose and dosage.

The invention is based, in part, on the results of a comparison of the efficacy of diclofenac solubilized with hydroxypropyl-beta-cyclodextrin to ketorolac and placebo for the treatment of moderate-to-severe post-surgical pain. The efficacy of diclofenac solubilized with hydroxypropyl-beta-cyclodextrin at several dose levels suggests a faster onset of action. Most notably, diclofenac formulated with hydroxypropyl-beta-cyclodextrin provides single-dose efficacy at about 50%, about 25%, about 12.5% and about 5% of the current recommended doses of diclofenac. This, in combination with the known human pharmacokinetic results for the formulation, supports reduced total daily doses of this NSAID with anticipated lower risk of toxicity by reducing the extent and duration of drug exposure. This is a novel finding and of clinical importance.

The minimum effective dose of diclofenac solubilized with hydroxypropyl-beta-cyclodextrin tested was 3.75 mg, demonstrating that diclofenac, if solubilized with hydroxypropyl-beta-cyclodextrin, may be administered at doses lower than those previously considered necessary for postoperative analgesia.

The term "diclofenac compound" refers to diclofenac or a pharmaceutically acceptable diclofenac salt. A pharmaceutically acceptable salt of diclofenac, can be an alkali metal salt, for example the sodium or the potassium salt, or the salt formed with an amine, e.g., a mono-, di- or tri-$C_1$-$C_4$ alkylamine, for example diethyl- or triethyl-amine, hydroxy-$C_2$-$C_4$ alkylamine, for example ethanolamine, or hydroxy-$C_2$-$C_4$ alkyl-$C_1$-$C_4$ alkylamine, for example dimethylethanolamine, or a quaternary ammonium salt, for example the tetramethylammonium salt or the choline salt of diclofenac (see, e.g., U.S. Pat. No. 5,389,681). Preferably the diclofenac salt is diclofenac sodium.

Suitable formulations of the present invention for parenteral administration include cyclodextrin inclusion complexes. One or more modified or unmodified cyclodextrins can be employed to stabilize and increase the water solubility and efficacy of compounds of the present invention. Useful cyclodextrins for this purpose include beta-cyclodextrins.

The term "beta-cyclodextrin" as used herein refers to cyclic alpha-1,4-linked oligosaccharides of a D-glucopyranose containing a relatively hydrophobic central cavity and hydrophilic outer surface. Particular efficacy has been observed in the present invention utilizing hydroxypropyl-beta-cyclodextrin, however, other substituted and unsubstituted beta-cyclodextrins can also be used in the practice of the invention. Additional examples of cyclodextrins that may be utilized are disclosed in U.S. Pat. Nos. 4,727,064, 4,764,604, 5,024,998, 6,407,079, 6,828,299, 6,869,939 and Jambhekar et al., 2004 Int. J. Pharm. 2004, 270(1-2) 149-66. The formulations may be prepared as described in U.S. Pat. Nos. 5,679,660 and 5,674,854.

The "pharmaceutical compositions" for use in accordance with the present invention can be formulated in any conventional manner using one or more pharmaceutically acceptable carriers or excipients. A "pharmaceutically acceptable" carrier or excipient, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

Pharmaceutical compositions include solid dosage forms, e.g., for perioral, transnasal (powder), or rectal (suppository) administration; and liquid dosage forms, e.g., for parenteral administration (injection), transnasal (spray), or perioral administration. In a specific embodiment, the pharmaceutical compositions of the present invention are liquid compositions formulated for intravenous or intramuscular administration, and particularly intravenous administration.

As used herein, the term "stabilizer" refers to a compound optionally used in the pharmaceutical compositions of the present invention in order to avoid the need for sulphite salts and increase storage life. Optimal stabilizers include antioxidants, specifically monothioglycerol and those described in U.S. Patent Publication 2005/0238674.

The term "dosage" is intended to encompass a formulation expressed in terms of mg/kg/day. The dosage is the amount of an ingredient administered in accordance with a particular dosage regimen. A "dose" is an amount of an agent administered to a subject in a unit volume or mass, e.g., an absolute unit dose expressed in mg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or doses of the formulation. The particular meaning in any case will be apparent from context.

The term "mammal" is intended to include, any warm-blooded vertebrate having the skin more or less covered with hair. Most preferably, the mammal is a human subject, but the mammal can also be a non-human animal. Thus, the invention is useful in veterinary medicine as well, e.g., for treating pain in a domestic pet, such as a canine or feline, a farm animal, a work animal, or an animal in a circus or zoological garden. The invention has particular value in treating pain in a horse, particularly in sport, such as thoroughbred and other race horses, rodeo horses, circus horses, and dressage horses. A particular advantage of the invention is that, by increasing the efficacy of a dosage of diclofenac, it is possible to administer a therapeutic dosage that is below a maximum allowed dose permitted by the particular regulatory authorities of the sport.

The term "minimum approved dose" refers to the minimum dosage that has received full regulatory approval by the appropriate United States or foreign regulatory authority as safe and effective for human or veterinary use.

The term "therapeutically effective" as applied to dose or amount refers to that quantity of a compound or pharmaceutical composition that is sufficient to result in a desired activity upon administration to a mammal in need thereof. As used herein with respect to the pharmaceutical compositions comprising an antifungal, the term "therapeutically effective amount/dose" refers to the amount/dose of a compound or pharmaceutical composition that is sufficient to produce an effective response upon administration to a mammal.

The term "amount" as used herein refers to quantity or to concentration as appropriate to the context. In the present invention, the effective amount of a compound refers to an amount sufficient to treat a patient/subject in need of analgesia. The effective amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

Methods of Treatment

As noted above, the novel dosage formulations of the invention are suitable for administering diclofenac to treat pain, i.e., for analgesia. Various embodiments of the invention provide for administration of unit doses to achieve a total dosage for the desired effect. The examples demonstrate efficacy of a 3.75 mg dose of diclofenac, which is about 5% of the minimum approved dose (and about 5% or about 2.5% of the approved daily dosage). However, this dose provides about 40% of the pain relief and one-third of the duration as the minimum approved dose. Better results can be achieved by selecting a dosage regimen with this dose of diclofenac, e.g., increasing the frequency of administration, to achieve a level and duration of pain relief acceptable for the patient. Higher dose formulations likewise could provide such relief. Such higher dose formulations are nevertheless lower than any approved formulation, and the dosage regimen results in administration of less diclofenac than the current approved minimum dosage regimen.

A significant advantage of the invention results from the ability to achieve efficacy with lower doses and overall daily dosing of diclofenac. Consequently, it is possible to reduce the dosage, and thus reduce toxicity.

In specific embodiments, the unit dose (i.e., the amount of active drug administered at one time to a patient) is no more than about 75%, no more than about 50%, no more than about 25%, no more than about 12.5%, and no more than about 5%, of the approved minimum dose. Doses that are about or greater than about 50% of the approved minimum dose can show the same level and duration of pain relieve as the minimum effective dose. Furthermore, by increasing the frequency of administration of a lower dose formulation, the patient can achieve the same levels of efficacy and duration of pain relief as with the approved doses, with decreased toxicity.

In another embodiment, then, the invention provides for titrating the dose reduction of diclofenac and beta-cyclodextrin by decreasing the unit dose to achieve an analgesic effect that is sufficient, even at a reduced level, for the patient's needs, which can be met by increasing the dosing frequency to achieve an effective daily dosage that is still lower than the minimum approved dose. The term "effect" means that there is a statistically significant difference in a response in patients taking the formulation containing the diclofenac relative to patients taking a placebo.

The formulations of the invention can be administered via any route, including parenteral, perioral, transnasal, and rectal. Particular parenteral routes of administration include intravenous and intramuscular injection.

The formulations of the invention are suitable for treating pain by administration either or both prophylactically and after onset of the pain. Thus, as used herein, the term "treat" (in any of its grammatical forms) means to reduce pain through administration of a formulation of the invention prior to or after the onset of pain, or both. In particular, the formulations are suitable in the treatment of acute painful conditions in humans and animals such as headache, including migraine, trauma, dysmenorrhoea, renal or biliary colic, post-operative pain, gout, arthritis, cancer related pain, musculoskeletal pain, lower back pain, fibromyalgia, and pain of infectious origin. Indeed, the low dosage of diclofenac will have little or no anti-inflammatory activity, so in the treatment of pain of infectious origin it will have little effect on any immune response to the infectious organism while achieving analgesia. In a specific embodiment, exemplified below, the formulation is effective to treat post-surgical dental pain resulting from surgical extraction of one or more third molars. In addition, although not intending to be bound by any particular mechanism of action, the formulation of the invention may be used prophylactically to prevent the formation of prostaglandins during and after surgery, with subsequent reduction in immediate post-operative pain. Further, the formulation of the invention may be used to modulate nuclear transcription factors, such as NF-κB, or to modulate ion channel activity, for example as described in Ocana, Maria et al., *Potassium Channels and Pain: Present Realities and Future Opportunities*, 500 Eur. J. Pharm. 203 (2004).

EXAMPLES

The present invention will be better understood by reference to the following Examples, which are provided as exemplary of the invention, and not by way of limitation.

Example 1

Analysis of Pain Relief Afforded to Patients Based on Administered Dose

A 336-patient, seven treatment arm, randomized, double-blind, single-dose, and placebo- and comparator-controlled, parallel-group study was conducted. Patients were randomly assigned to receive a single dose of either diclofenac sodium solubilized with hydroxypropyl-beta-cyclodextrin (hereinafter "DIC"), ketorolac tromethamine, or placebo.

Bolus IV injectable 2 ml solutions were prepared by solubilizing diclofenac sodium with hydroxypropyl-beta-cyclodextrin. The formulation strengths were as follows:

| Formulation: | Diclofenac sodium solubilized with hydroxypropyl-β-cyclodextrin |
|---|---|
| Strengths: | 75 mg, 37.5 mg, 18.75 mg, 9.4 mg and 3.75 mg |
| Dosage: | Bolus IV injection (no less than 15 sec) |
| Batch Number: | 063004 (PPS04010) |
| Manufacturer: | Manufactured for Javelin by Precision Pharma |
| Storage Conditions: | Room temperature |

Active Control/Comparator:

| Formulation: | Ketorolac Tromethamine |
|---|---|
| Strength: | 30 mg |
| Dosage: | Bolus IV injection (no less than 15 sec) |
| Batch Number: | 21-430-DK |
| Manufacturer: | Abbott Labs |
| Storage Conditions: | Room temperature |

Pain was assessed by each patient at Baseline (0 hour: Visual Analog Scale (VAS) and categorical pain intensity only), at 5, 15, 30 and 45 minutes, and at 1, 1.5, 2, 3, 4, 5, 6, 7, 8, 10, 12 and 24 hours after administration of study medication and immediately prior to the first dose of rescue medication. At each post-dose time period, levels of pain intensity (categorical and VAS) and pain relief (categorical and VAS) was assessed by each patient. Patients were also provided with 2 stopwatches to measure perceptible and meaningful pain relief.

The presence of a dose-response was tested with a step-down testing procedure. Total pain relief (TOTPAR), peak pain relief, pain intensity difference (SPID), summed peak reduction in pain intensity difference (SPRID), and patient global evaluation was analyzed with analysis of variance (ANOVA) with treatment, center, and baseline categorical pain intensity as factors. The possibility of interactions was investigated. Comparisons of the DIC groups with the placebo and Ketorolac groups were performed with Dunnett's test. The presence of a linear dose response for the ordered DIC dose levels was tested with orthogonal contrasts for TOTPAR, SPID and SPRID. Tests of individual DIC dose levels versus placebo for TOTPAR, SPID, and SPRID were conducted with the Tukey, Ciminera, and Heyse step-down testing procedure. The mean, standard deviation, and sample size were presented for each treatment group. Significant p-values (those less than or equal to 0.05) were presented for each step of the procedure. Non-significant p-values were represented with three dashes. Time to onset of perceptible relief and time to onset of meaningful relief was analyzed with survival analysis techniques. These variables were summarized with number of observations, mean, standard deviation, median, and range. Log-rank tests were used to compare treatments with respect to survival distributions. The median time to event for each treatment group was estimated with the Kaplan-Meier product limit estimator. A 95% confidence interval for each estimated median time to event was calculated.

The results of the study were strongly positive, novel and could not have been anticipated from prior experience with diclofenac. The doses had been chosen based on the currently recommended minimally effective doses of 1 mg/kg (50 mg immediate-release or 100 mg sustained-release orally or 75 mg intramuscularly or intravenously). Based on these doses the test conditions were a full dose (75 mg), half dose (37.5) mg, a possibly effective dose (18.75 mg) and two placebo doses (9.75 & 3.4 mg). The findings were as follows:

TABLE 1

TOTPAR (Sum of Pain Relief VAS 0-100 mm ratings 0-6 hours)

| Treatment Group | Result | % Maximum Effect |
| --- | --- | --- |
| Placebo | 62.8 (SEM 9) | 17% |
| DIC 3.75 mg | 134.1 (SEM 8) | 38% |
| DIC 9.4 mg | 237.6 (SEM 15) | 68% |
| DIC 18.75 mg | 284.4 (SEM 21) | 82% |
| DIC 37.5 mg | 348.2 (SEM 30) | 100% |
| DIC 75 mg | 346.3 (SEM 27) | 100% |
| ketorolac | 400.3 (SEM 36) | 100% |

See FIG. 1 for the corresponding graphical representation of the pain relief afforded to patients based on the formulation strengths administered.

Example 2

Analysis of Efficacy & Duration of Pain Relief at Lower Doses of Diclofenac

Figure 2:
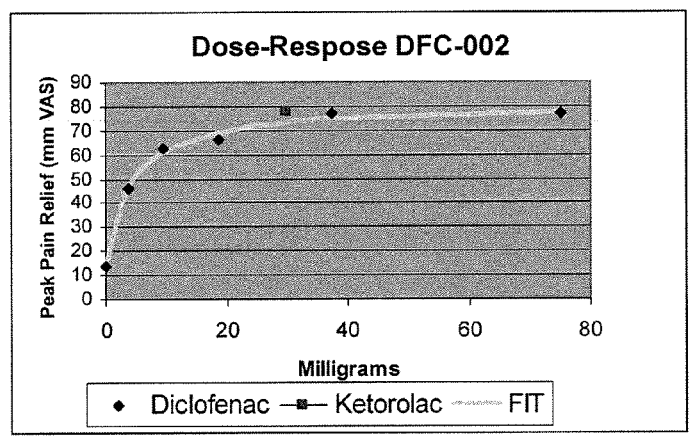
FIG. 2 illustrates the dose-response curve for peak analgesia observed (mm VAS) over mg of formulation. Both diclofenac and ketorolac formulations were tested.

To explore this further, the dose-duration relationship in the same study was examined using the median time to remedication in the single-dose phase. Utilizing the results of study in Example 1, the efficacy and duration of pain relief were thoroughly analyzed. The lowest IV dose of DIC (3.75 mg) had 38% of the effect of the maximal dose, and the next lowest dose (9.4 mg) had 68% of the maximal possible effect, despite being 5% and 12% respectively of the current recommended minimally effective dose (1 mg/kg). FIG. 2 contains a graphical illustration of the dose-response for peak analgesia observed in the study.

Figure 3:
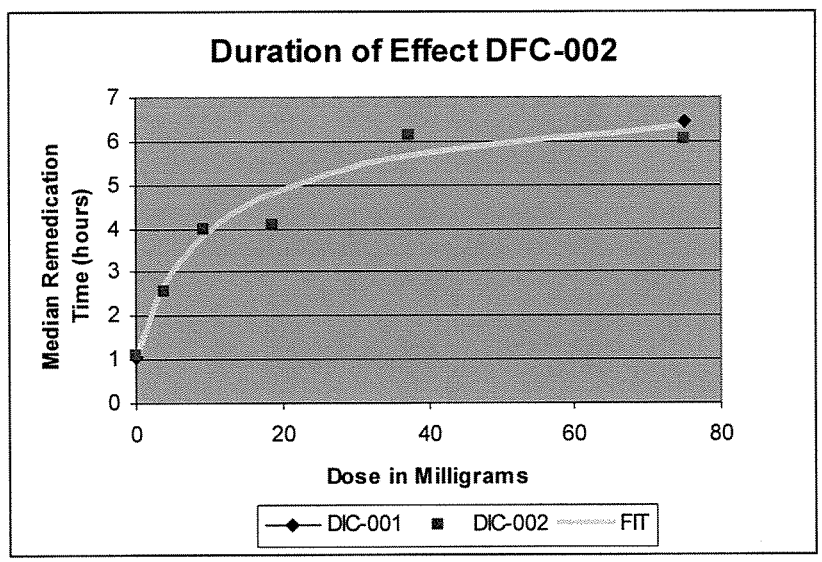
FIG. 3 illustrates the dose-duration relationship examined using the median time to re-medication (hours) in the single dose phase. Two formulations of diclofenac were studied.
Figure 4:
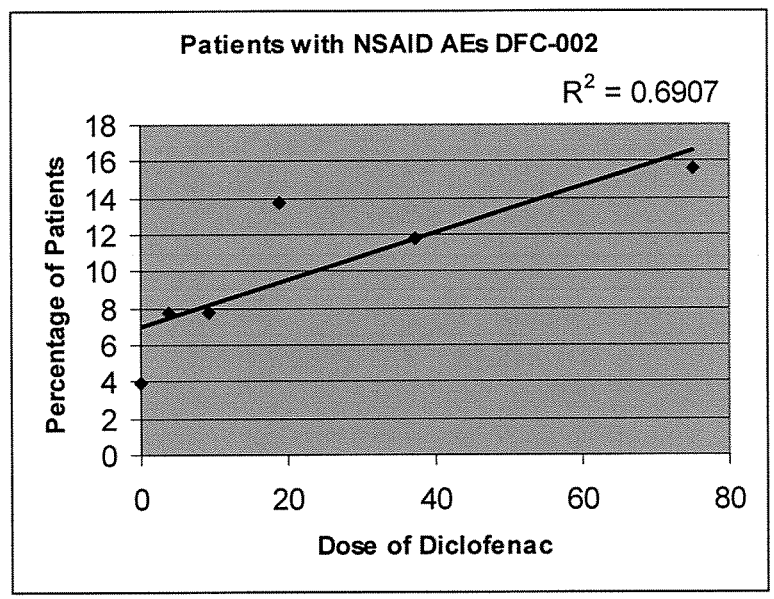
FIG. 4 illustrates the percentage of patients with NSAID Adverse Events by dose of diclofenac (mg).

FIG. 3 depicts the dose-duration relationship examined using the median time to remedication in the single dose phase. The peak analgesic response was about 80% pain relief, with a 50% response at a dose of 4-8 milligrams of Diclofenac in relation to dental pain. Similar peak analgesic response was seen for 30 milligrams of ketorolac. Given the shape of the dose response curve, it is clear that lower doses of the DIC formulation achieved the same results as the current established dose of diclofenac of 75 milligrams.

The findings show a 6 hour duration of effect for all doses above about 20 milligrams (18 milligrams).

For most drugs the findings of significant activity at doses far below the recommended doses would be of little significance due to large therapeutic indices (wide ranges between the effective and toxic doses). The opposite is true for parenteral NSAIDs; it has been well established in the prior art that increasing the dose of these drugs rapidly diminishes their utility due to increasing risk of toxicity.

Thus the finding that with the new formulation of diclofenac that 5%-12% of the usual dose can provide 38-68% of the desired therapeutic effect is remarkable and unanticipated. This leads to the possibility that the high early blood levels possible with the new formulation allow lower total daily doses resulting in less risk of toxicity.

This finding demonstrates efficacy with a lower daily dose (25-75 mg/day) than current dosing of diclofenac (75-200 mg/day), and anticipates better dosing paradigms (less than Q 12 hours) offering the expectation of lesser toxicity. Proof of lesser toxicity from available data from this study is suggestive, based on the known relationship of dose and toxicity.

The novel diclofenac formulation allowed by hydroxypropyl-β-cyclodextrin has been shown to provide proof of single-dose efficacy at 50%, 25%, 12.5% and 5% of the current recommended doses of diclofenac. This in combination with the known human pharmacokinetic results for the formulation supports reduced total daily doses of this NSAID with anticipated lower risk of toxicity by reducing the extent and duration of drug exposure.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications publications product descriptions, and protocols are cited throughout this application the disclosures of which are incorporated herein by reference in their entireties for all purposes.

What is claimed is:

1. A method for treating a mammal in need of analgesia, comprising administering a pharmaceutical composition comprising:
   (a) a unit dose of diclofenac sodium effective to induce analgesia; and
   (b) a beta-cyclodextrin compound;
   (c) a stabilizer;

wherein the unit dose of the diclofenac sodium is between about 3.75 mg to about 9.4 mg; and wherein the pharmaceutical composition is formulated for parenteral administration.

2. A method for treating a mammal in need of analgesia, comprising administering a pharmaceutical composition comprising:
  (a) a unit dose of diclofenac sodium effective to induce analgesia;
  (b) a beta-cyclodextrin compound; and
  (c) a stabilizer; wherein the unit dose of the diclofenac sodium is less than about 5 mg; and wherein the pharmaceutical composition is administered parenterally, wherein parenteral administration refers to intravenous administration or intramuscular administration.

3. A method for treating a mammal in need of analgesia, comprising administering a pharmaceutical composition to the mammal in need thereof, wherein the pharmaceutical composition comprises:
  (a) a unit dose of diclofenac sodium effective to induce analgesia; and
  (b) a beta-cyclodextrin compound;
  (c) a stabilizer;
  wherein the unit dose of the diclofenac sodium is less than 10 mg; and
  wherein the pharmaceutical composition is administered intravenously.

4. A method for treating a mammal in need of analgesia, comprising administering a pharmaceutical composition to the mammal in need thereof, wherein the pharmaceutical composition comprises:
  (a) a unit dose of diclofenac sodium effective to induce analgesia; and
  (b) a beta-cyclodextrin compound;
  (c) a stabilizer;
  wherein the dose of the diclofenac sodium is less than 5 mg (+/−20%); and
  wherein the pharmaceutical composition is administered intravenously.

* * * * *